United States Patent

Ploug et al.

[11] Patent Number: 6,120,736
[45] Date of Patent: Sep. 19, 2000

[54] ANALYSIS APPARATUS

[75] Inventors: Ole Ploug, Allerød; Jacob Bøgh Poulsen, København, both of Denmark

[73] Assignee: Danfoss A/S, Nordborg, Germany

[21] Appl. No.: 08/913,575

[22] PCT Filed: Feb. 29, 1996

[86] PCT No.: PCT/DK96/00086

§ 371 Date: Sep. 4, 1997

§ 102(e) Date: Sep. 4, 1997

[87] PCT Pub. No.: WO96/27801

PCT Pub. Date: Sep. 12, 1996

[30] Foreign Application Priority Data

Mar. 4, 1995 [DE] Germany ............... 195 07 638

[51] Int. Cl.[7] .................................................. G01N 33/00
[52] U.S. Cl. .................. 422/81; 422/64; 422/68.1; 422/103; 436/52
[58] Field of Search .................... 422/81, 63, 64, 422/68.1, 103; 436/52, 54

[56] References Cited

U.S. PATENT DOCUMENTS 5,250,263 10/1993 Manz ......................... 422/81

Primary Examiner—Lyle A. Alexander
Attorney, Agent, or Firm—Lee, Mann, Smith, McWilliams, Sweeney & Ohlson

[57] ABSTRACT

An analysis apparatus (1) for carrying out chemical analyses is disclosed, having a base member (3) in which there is at least one channel (8, 9), and having at least one functional element (12) which is in fluid or gaseous connection with the channel. In such an apparatus, it is desirable to facilitate maintenance and increase flexibility. For that purpose, the functional element (12) is positioned on the outside of the base member (3) and is in connection with the channel (8, 9) by way of at least one interface opening (10, 11).

8 Claims, 2 Drawing Sheets

ANALYSIS APPARATUS

BACKGROUND OF THE INVENTION

The invention relates to an analysis apparatus for carrying out chemical analyses having a base member in which there is at least one channel, and having at least one functional element which is in fluid or gaseous connection with the channel.

In certain chemical analyses, a chemical sample that is able to flow is mixed with at least one reagent. The reagent reacts with the sample. A resulting reaction product, for example, a colour change, can then be detected by a detector.

To control the route from sample to reagent, U.S. Pat. No. 5,250,263 describes an analysis apparatus which essentially consists of a plurality of plates which are layered one above another in the manner of a stack. In each plate there are channels in the form of grooves in one of the surfaces, bores or openings which together form with a plate arranged thereover longitudinally or transversely running channels or reaction chambers. Furthermore, between individual plates there are provided membranes which can be acted on with compressed air through separate channels. These membranes then act as pumps. Valves which control the path of the fluids through the channels, for example, preventing a back flow, are also provided in some plates.

Such an apparatus can be of relatively compact construction, which has the advantageous effect that the necessary amounts of sample and reagent can be kept relatively small. Certain problems arise in handling, however, because the functional elements, for example, the valves and the pumps, are virtually inaccessible for maintenance. If such a functional element is defective, it is frequently the case that the entire apparatus must be exchanged. Moreover, in an experimental environment it is relatively difficult to undertake changes, for example, in respect of the characteristics of the pumps or the valves, because to do so the apparatus has to be virtually completely destroyed. Since there are a number of channels which are formed by successive bores, it is virtually impossible on assembly to repeat the same flow-through characteristics of these channels. Even small shifts in the individual plates relative to one another cause irregularities in the walls of these channels, which change the flow conditions there. Provided that only a few stages are affected, this can be tolerated. In the case of the described large number of superimposed plates, however, satisfactory reproducibility is very unlikely. In practice, components cannot be exchanged.

SUMMARY OF THE INVENTION

The invention is based on the problem of providing an analysis apparatus in which maintenance is simplified and which is distinguished by a modular construction, the manufacture of which is simple and which is versatile and robust in operation.

That problem is solved in an analysis apparatus of the kind mentioned in the introduction in that the functional element is positioned on the outside of the base member and is in connection with the channel by way of at least one interface opening.

In this manner the conduction paths are separated from the functional elements from construction onwards. The conduction paths or channels (in most cases several channels will be provided) are located in the base member. The base member is formed from a rigid material which does not yield when subjected to the pressures prevailing in the channels and thus guarantees that the volume of the channels will be constant. The functional elements, for example, pumps, valves or detectors, are located on the outside. They can be compared with a printed circuit board in electronics, where the individual printed conductors are provided on the printed circuit board whilst the electrical or electronic components, such as transistors, resistors, capacitors and so on, are mounted on the printed circuit board and electrically connected to the printed conductors. The connection between base member and functional element is effected by way of an interface opening, that is, a defined point, at which the channel or a part branching therefrom is lead to the surface of the base member. An opening in the functional element is correspondingly matched so that transport of fluid or gas from the base member into the functional element or vice versa is possible. Because the functional element is positioned externally on the base member, it can be exchanged without difficulty. This has advantages during repair or maintenance. A defective part can easily be exchanged. At the experimental stage it is possible to try out different functional elements at the same point or find out which element or what size of element is best suited. Construction is such that production also is simplified.

In a preferred construction, the base member comprises a stack of plates comprising at least two adjacent plates, in the area of contact of which the channel is formed, at least one plate having on its free surface a mounting area for the functional element. The interface openings are arranged in this mounting area. At the same time, however, it is possible to secure the functional element to the base member here, so that coordination of the interface openings with the functional element can be ensured in a simple manner.

The base member preferably comprises several parts, each part having a main flow direction and the main flow directions of at least two parts differing from one another. In this manner, channels which run mainly in one direction can be arranged in one part whilst channels that run transversely thereto can be arranged in another part. This facilitates construction quite considerably because intersection problems are largely avoided. Moreover, this construction has the advantage that between the individual channels sufficient material can be left in the base member for the ability of the channels to resist pressure to be increased. In particular, in each part a plurality of channels can be arranged parallel to one another and can be combined virtually as desired with one another by different linkages in another part. An analysis apparatus which can be adapted to many requirements is obtained using simple basic equipment.

Versatility is yet further improved in that the analysis apparatus is of modular construction and comprises at least one tank module, an evaluation module and a pump module. By simple exchange of one or several modules the analysis apparatus can be readily adapted to a desired application.

Here, the base member preferably forms the pump module. The pump or pumps that are required to set the individual fluids and gases moving in order to mix them with one another or to bring them to a different location are here arranged on the base member. The base member is in most cases of a more mechanically stable construction that other modules anyway, because it is used as carrier for the other modules. This increased mechanical stability can then also be exploited to carry the pumps, because experience shows that the highest pressures are to be expected in the immediate vicinity of the pumps.

Mutually-associated modules preferably lie with interfaces adjacent to one another. These interfaces represent on the one hand the fluid connections between individual modules and provide on the other hand an opportunity to join two modules mechanically.

The tank module preferably has a mounting and a connection for at least one tank. The reagent, a cleaning fluid or a carrier fluid can be contained in such a tank. Because the tank module has not only a connection but also a mounting for the tank, not only is the transport of fluid from the tank to the other parts of the analysis apparatus ensured, but also the mechanical fixing of the tank.

In an especially preferred construction, the connection is in the form of a quick-release coupling. Exchange of a tank, for instance when the tank is emptied, can be effected relatively quickly.

It is also preferred for the connection to comprise a tank-piercing device. As the tank is inserted, it is thus simultaneously opened. This reduces the time taken for tank change. Tank change is additionally facilitated in that the piercing device makes a hole in the bottom of the tank so that fluid is able to flow out. There is therefore no need for an opened tank to be tilted or emptied out.

The pump module preferably comprises at least one valve. This enables the fluid path to be controlled in the vicinity of the pump.

The pump module preferably comprises several pumps which are arranged in several rows offset with respect to one another. The channels in the pump module can therefore be moved closer together because there is no longer any requirement to leave sufficient space between the individual channels for a pump to fit between them.

It has proved useful for the evaluation module to comprise at least one detector. The detector can function in known manner, for example, optically, ion-selectively or electrochemically. Evaluation is then carried out directly in the apparatus.

It is herein especially preferred for the detector to be arranged in a detector module which is connected to the evaluation module. In this manner, the detector too can be easily exchanged, without requiring further parts to be exchanged. The analysis apparatus can thus be readily adapted to different requirements.

The evaluation module preferably comprises a sample-removal channel. The sample is therefore supplied to the evaluation module immediately. This keeps the time taken to transport the sample through the apparatus short, so that the response or reaction times can be kept correspondingly short.

The evaluation module advantageously has a mixing point which is connected to the sample-removal channel by way of a pump. This pump, which, as an exception, is not arranged on the pump module, conveys the sample to the mixing point. Mixing of the sample with the reagent can therefore be controlled relatively accurately.

A reaction channel module is preferably connected to the evaluation module. The reaction channel too can then be exchanged relatively quickly. For example, reaction channels of different lengths can be used, so that even as regards the reaction channel, adaptation to different conditions can be achieved relatively easily.

BRIEF DESCRIPTION OF THE DRAWINGS

The invention is described hereinafter with reference to a preferred embodiment in conjunction with the drawings, in which.

DESCRIPTION OF THE PREFERRED EMBODIMENT

Figure 2:
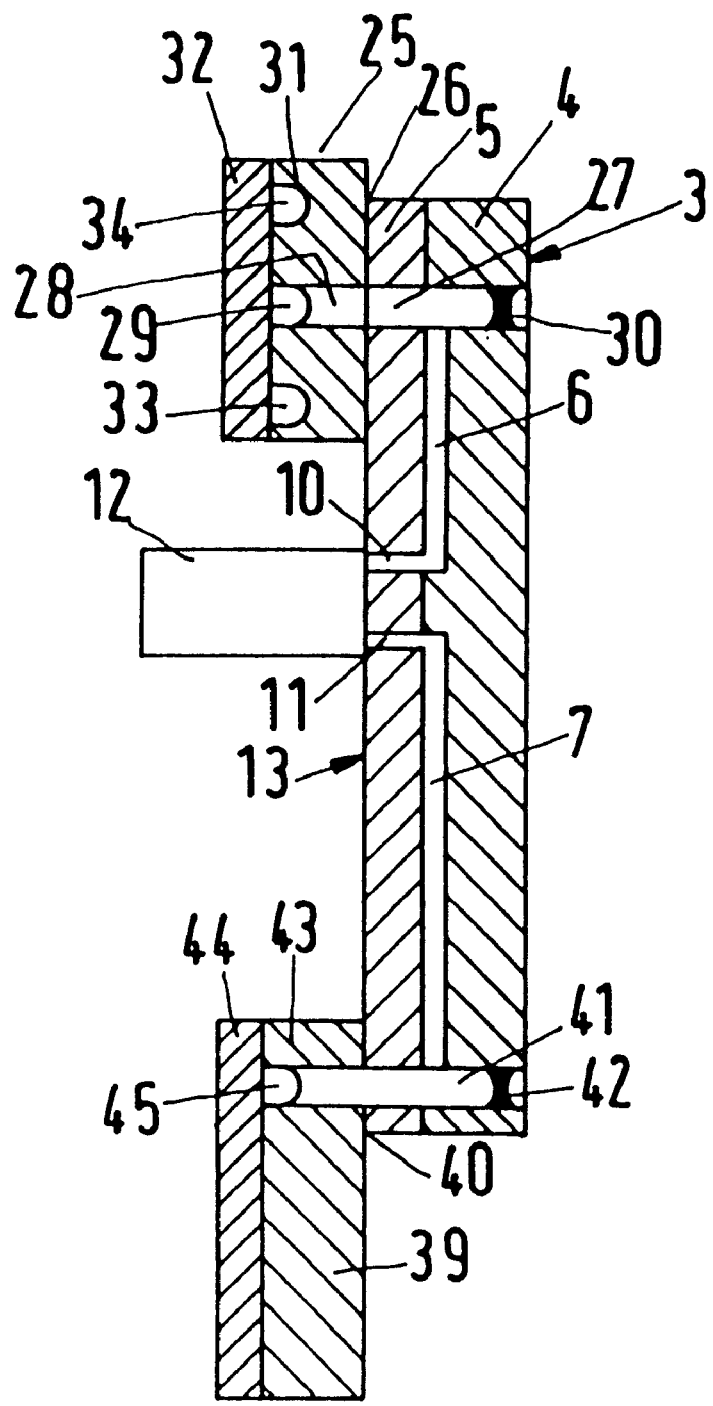
FIG. 2 is a partial section II—II of FIG. 1.

An analysis apparatus 1 is arranged in a housing 2. The analysis apparatus 1 has a base member 3 in the form of a stack of plates, the construction of which is shown in FIG. 2.

Figure 1:
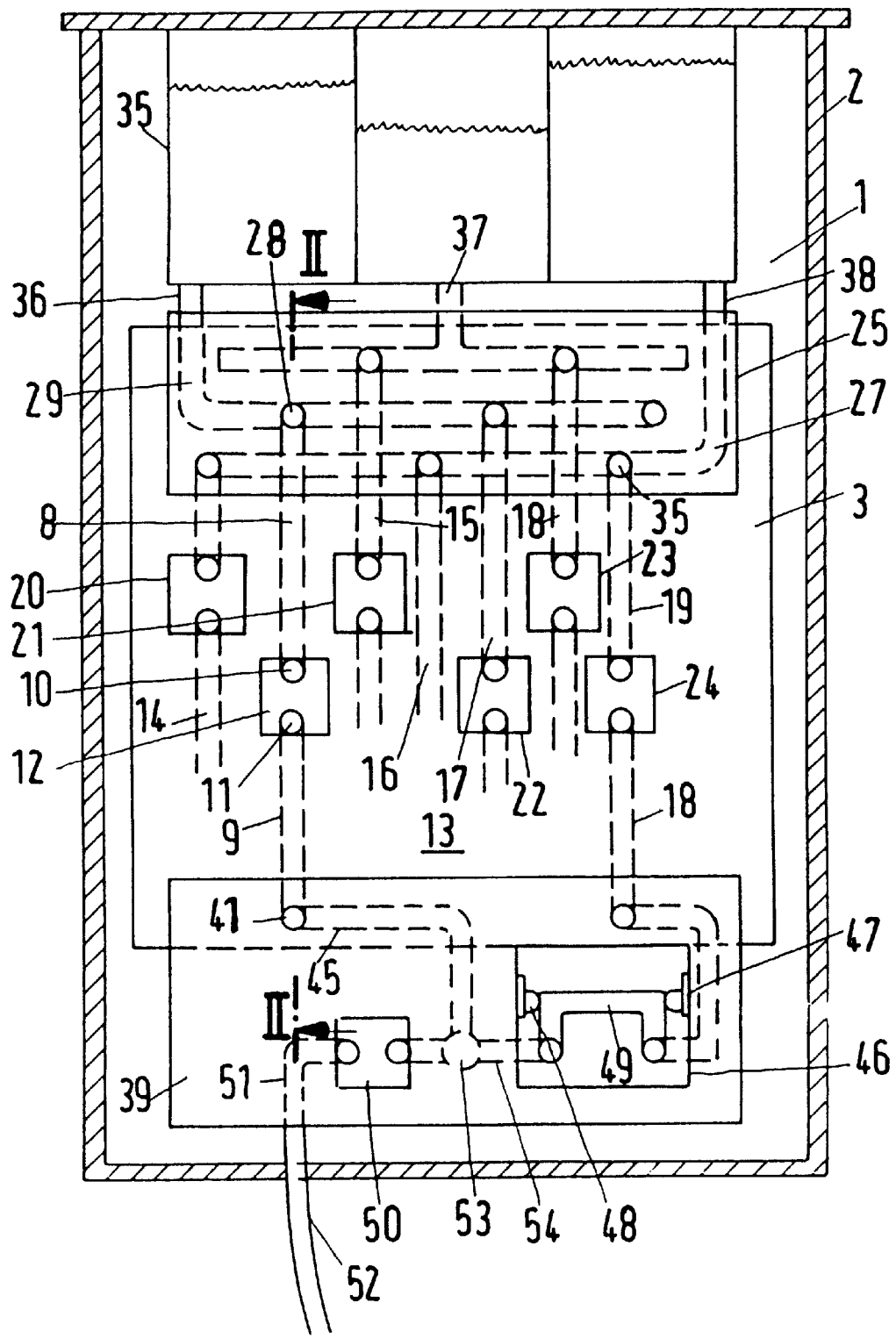
FIG. 1 is a diagrammatic sectional view of an analysis apparatus.

The base member 3 consists in this particular case of two plates 4, 5, one plate 4 having grooves 6, 7 in its face that contacts the other plate 5; the grooves can be created by milling or etching or, through the shaping of a corresponding casting mould, as such a plate is being cast. These grooves 6, 7 are covered by the other plate 5, thus creating channels 8, 9 (FIG. 1). To support the plates, they can be secured to a solid supporting plate. This is advantageous if the plates 4 and 5 are manufactured from a relatively soft plastics material.

The other plate 5 has interface openings 10, 11 which are in connection with the channels 8, 9. A pump 12, in connection by way of the interface openings 10, 11 with the channels 8, 9, is arranged on this plate 5. The pump 12 is therefore positioned on the base member 3 or, more accurately, on the plate 5, from the outside. For that purpose a mounting area 13, on which the pump 12 can be not merely positioned but also secured, is provided on the plate 5.

As is apparent from FIG. 1, several substantially parallel channels 8, 14–19 are provided in the base member 3, most channels 8, 14–19 being associated with a pump 12, 20–24, all of which are arranged in the mounting area 13 of the base member 3. The pumps 12, 20–24 are, in an identical manner, in connection with the channels 8, 14–19 through interface openings, as illustrated for pump 12 in FIG. 2.

In the embodiment illustrated, the pumps 12, 20–24 are arranged in two rows, the pumps in the two rows being offset with respect to one another. They are therefore arranged staggered, as it were. The individual channels 8, 14–19 can thus be arranged closer than would on the whole be possible given the width of the pumps 12, 20–24.

Valves or other functional elements can be positioned on the base member 3 in place of pumps, and can then be connected by way of corresponding interface openings to the channels.

Because it is equipped with pumps, the base member 3 can also be referred to as the pump module.

Positioned on the base member 3 in the region of its upper end is a tank distributer 25, which adjoins the base member 3 by way of an interface 26. In the interface there are again interface openings 27 in the plate 5 which interface openings are in connection with corresponding openings 28 in the tank distributer 25. A channel 29 in the tank distributer 25 is connected to the channel 8 by way of the interface opening 28. The interface opening 27 can also be created by a continuous bore in the base member 3 which is closed by a stopper 30.

The tank module 25 likewise comprises a stack of plates 31, 32, the plate 31 being formed with grooves which become channels 29, 33, 34 when covered by the plate 32.

The tank module 25 has at its upper end a mounting 35 and at least one connection, three connections 36, 37, 38 in the embodiment illustrated, for fluid tanks. Three tanks having different fluid levels are illustrated inserted in the mounting 35. The mounting 35 can also be placed immediately adjacent to the tank module 25. The offset was chosen in this particular illustration in order to be able to show the connections 36, 37, 38. The mounting 35 can also itself be constructed as a tank and receive fluids directly.

The connections 36, 37, 38 are preferably constructed as quick-release locks. They can have an upwardly pointing needle or another piercing device so that basically the respective tank merely needs to be inserted from above into the mounting 35. The needle pierces its opening and the fluid contained therein is able to flow out downwards.

At the lower end of the base member 3, arranged in a similar way to the tank module 25, is an evaluation module 39, which lies adjacent to the base member 3 by way of a further interface 40. Again, in the interface 40 there is an interface opening 41 which is in the form of a through-bore and is closed by stopper 42. Through this interface opening 41 fluid is able to flow from the channel 9 into the evaluation module 39. The evaluation module 39 is also constructed from two plates 43, 44; grooves provided in plate 43 form channels 45 when covered by the other plate 44.

As can be seen in FIG. 1, a detector module comprising an optical detector 47, 48 with a measuring path 49 is positioned externally on the evaluation module 39. Because the detector module 46 is likewise positioned from the outside on the evaluation module 39, the detector is readily exchangeable.

Furthermore, a pump 50 which is able to draw a sample fluid by way of a sample-removal channel 51 from a connection 52 is arranged on the evaluation module 39. The manner in which the sample is obtained is known per se, and is not therefore described further.

Finally, a mixing point 53 into which the channel 45 opens is provided in the evaluation module 39, and is moreover charged with fluid from the pump 50.

A reaction channel 54 is arranged between the mixing point 53 and the input to the detector module 46. This reaction channel is illustrated inside the evaluation module 39. The reaction channel can alternatively be taken out of the evaluation module 39 and housed in a separate component, which in turn is positioned on the evaluation module 39.

Such an analysis apparatus can operate, for example, according to the principle of the flow-injection analysis system (FIA). Here, using one of the pumps a flow is produced from the tank module through the channel 45, the mixing point 53, the detector module 46 and the channel 19 having the pump 24 back to a different tank. At intervals the pump 50 feeds a defined sample amount into the mixing point 53 and the resulting reaction of the sample with the continuously flowing reagent fluid is determined in the detector module 46.

The analysis apparatus preferably operates, however, as a continuous flow analysis system (CFA). In that case there is a small flow of reagent fluid. The pump 50 draws a defined amount of sample fluid from the connection 52 and conveys this amount to the mixing point 53. At the same time reagent from connection 36 is conveyed to the mixing point 53, for example, by way of the pump 12. At the mixing point the sample fluid conveyed by the pump 50 reacts with the reagent fluid and the mixture is passed through the channel 54 into the detector module 46. The detector module evaluates, for example, changes in colour. The pump 24 then pumps the fluid out of the detector module 46 into a waste tank, for example, by way of the connection 38.

As is shown particularly in FIG. 1, the main flow direction of the fluids in the member 3 is primarily from top to bottom and from bottom to top, whilst the main movement direction of the fluid in the tank module 25 is from left to right and from right to left. Through the use of different modules it is therefore possible to ensure that the channels run substantially in straight lines. Intersections are largely avoided within a module. This produces clearly defined flow conditions, which are particularly desirable in an analysis according to the CFA system.

As can be seen, a different configuration of the individual channels can be achieved relatively quickly by exchanging the tank module 25. Because they are arranged on the outside of the base member, the pumps can be quickly exchanged, which is advantageous firstly for maintenance and secondly also at an experimental stage when one is not yet certain what pump or what pump size is correct.

What is claimed is:

1. An analysis for carrying out chemical analyses, comprising a base member having at least one channel, at least one functional element being in fluid or gaseous connection with the channel, the functional element being positioned on an exterior surface of the base member being in connection with the channel by means of at least one interface opening, the base member comprising a stack of plates with at least two adjacent plates having a contact area, the channel being formed in the contact area, at least one plate comprising a mounting plate and having a mounting area for the functional element, the base member having at least one pump module mounted thereon as a said functional element, at least one tank module and one evaluation module being connected with the pump module, the modules bearing on the exterior surface of the mounting plate with interface surfaces, and each module having a main flow direction, the main flow direction of at least two modules differing from each other.

2. An apparatus according to claim 1, in which the pump module includes at least one valve.

3. An apparatus according to claim 1, in which the pump module includes a plurality of pumps which are arranged in several rows the pumps in each row being offset with respect to the pumps in each adjacent row.

4. An apparatus according to claim 1, in which the tank module has a tank mounting and a connection for at least one tank.

5. An apparatus according to claim 4, in which the connection comprises a quick-release coupling and having a tank-piercing device.

6. An apparatus according to claim 1, in which the evaluation module includes at least one detector which is located in a detector module.

7. An apparatus according to claim 6, in which the evaluation module includes a sample-removal channel.

8. An apparatus according to claim 7, in which the evaluation module has a mixing point which is connected to the sample-removal channel.

* * * * *

UNITED STATES PATENT AND TRADEMARK OFFICE
CERTIFICATE OF CORRECTION

PATENT NO. : 6,120,736
DATED : September 19, 2000
INVENTOR(S) : Ole Ploug, et al.

It is certified that error appears in the above-identified patent and that said Letters Patent is hereby corrected as shown below:

On the title page, item [73] Assignee, should read:

--Danfoss A/S. Denmark, Germany --.

Signed and Sealed this

Eighth Day of May, 2001

*Attest:*

NICHOLAS P. GODICI

*Attesting Officer*  *Acting Director of the United States Patent and Trademark Office*

UNITED STATES PATENT AND TRADEMARK OFFICE
CERTIFICATE OF CORRECTION

PATENT NO. : 6,120,736
DATED : September 19, 2000
INVENTOR(S) : Ole Ploug, et al.

It is certified that error appears in the above-identified patent and that said Letters Patent is hereby corrected as shown below:

<u>Title page</u>,
Item [73] Assignee, should read:

-- Danfoss A/S. Nordborg, Denmark --.

Signed and Sealed this

Thirtieth Day of October, 2001

Attest:

*Nicholas P. Godici*

NICHOLAS P. GODICI
*Attesting Officer*   *Acting Director of the United States Patent and Trademark Office*